United States Patent
Desenne et al.

(10) Patent No.: US 8,722,029 B2
(45) Date of Patent: May 13, 2014

(54) COMPOSITION CONTAINING AT LEAST ONE VOLATILE LINEAR ALKANE, AT LEAST ONE SILICONE AND AT LEAST ONE FATTY SUBSTANCE

(75) Inventors: Patricia Desenne, Pringy (FR); Laurent Chesneau, Levallois (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 12/975,705

(22) Filed: Dec. 22, 2010

(65) Prior Publication Data

US 2011/0150811 A1    Jun. 23, 2011

Related U.S. Application Data

(60) Provisional application No. 61/296,487, filed on Jan. 20, 2010.

(30) Foreign Application Priority Data

Dec. 23, 2009    (FR) ...................................... 09 59556

(51) Int. Cl.
*A61K 8/02*    (2006.01)
(52) U.S. Cl.
USPC ...................................................... 424/70.12
(58) Field of Classification Search
None
See application file for complete search history.

(56) References Cited

U.S. PATENT DOCUMENTS

| 8,025,869 B2 * | 9/2011 | Yu | 424/61 |
| 2006/0292096 A1 * | 12/2006 | Yu | 424/64 |
| 2008/0269352 A1 * | 10/2008 | Falkowski et al. | 514/762 |
| 2010/0015073 A1 * | 1/2010 | Clavel et al. | 424/63 |

FOREIGN PATENT DOCUMENTS

| DE | 10 2008 012 457 | 12/2008 |
| EP | 1 093 806 | 4/2001 |
| EP | 1 093 808 | 4/2001 |
| EP | 1 093 809 | 4/2001 |

OTHER PUBLICATIONS

French Search Report issued Oct. 21, 2010, in FR 09 59556, filed Dec. 23, 2009.
U.S. Appl. No. 12/977,183, filed Dec. 23, 2010, Desenne, et al.
U.S. Appl. No. 12/969,980, filed Dec. 16, 2010, Desenne, et al.
U.S. Appl. No. 12/970,988, filed Dec. 17, 2010, Desenne, et al.
U.S. Appl. No. 12/977,257, filed Dec. 23, 2010, Desenne, et al.
U.S. Appl. No. 12/977,204, filed Dec. 23, 2010, Desenne, et al.
U.S. Appl. No. 12/977,227, filed Dec. 23, 2010, Desenne, et al.
U.S. Appl. No. 12/975,632, filed Dec. 22, 2010, Desenne, et al.

* cited by examiner

*Primary Examiner* — Anand Desai
*Assistant Examiner* — Melissa Mercier
(74) *Attorney, Agent, or Firm* — Oblon, Spivak, McClelland, Maier & Neustadt, L.L.P.

(57) ABSTRACT

Composition containing, in an aqueous medium:

from 0.1% to 20% by weight of one or more volatile linear alkanes, from 0.5% to 25% by weight of one or more silicones having a viscosity of greater than or equal to 20 000 $mm^2/s$, one or more non-silicone fatty substances, in a weight ratio of non-silicone fatty substance(s)/silicone(s) having a viscosity of greater than or equal to 20 000 $mm^2/s$ of less than or equal to 5. Use thereof for the cosmetic treatment of keratin materials, preferably keratin fibers such as the hair.

20 Claims, No Drawings

COMPOSITION CONTAINING AT LEAST ONE VOLATILE LINEAR ALKANE, AT LEAST ONE SILICONE AND AT LEAST ONE FATTY SUBSTANCE

REFERENCE TO PRIOR APPLICATIONS

This application claims priority to U.S. provisional application Ser. No. 61/296,487, filed Jan. 20, 2010; and to French patent application 09 59556, filed Dec. 23, 2009, both incorporated herein by reference.

FIELD OF THE INVENTION

The present invention relates to a composition comprising, in an aqueous medium, one or more volatile linear alkanes, one or more high-viscosity silicones, and one or more non-silicone fatty substances preferably in particular proportions, to the use thereof for the cosmetic treatment of keratin materials, preferably keratin fibres such as the hair, and to a method for cosmetic treatment of keratin materials using said composition.

BACKGROUND OF THE INVENTION

In the field of hair treatment, the use of volatile solvents is known in leave-in or rinse-out hair care products. They are generally used for various reasons. They make it possible in particular to modify the sensory effect of a hair product by giving it a light and non-tacky texture in the hand. They can also give it a slippery nature which facilitates distribution of the product on the hair and in particular on dry hair.

In aqueous emulsions of the oil-in-water type, which can be in the form of more or less gelled creams, the addition of volatile solvents can also make it possible to solubilize silicone gums which, by virtue of their intrinsic viscosity, would be difficult to incorporate into the compositions.

These volatile solvents, which are generally liquid fatty esters, hydrocarbon-based oils of isododecane or isohexadecane type, and/or silicone oils, can in particular cause problems of a greasy feel, a lack of sheen, and stiff, hard hair.

There remains therefore a need to replace these volatile solvents in order to avoid the abovementioned drawbacks.

DETAILED DESCRIPTION OF THE PREFERRED EMBODIMENTS

It has now been discovered, unexpectedly and surprisingly, that combining one or more volatile linear alkanes, one or more high-viscosity silicones and one or more non-silicone fatty substances in particular proportions in an aqueous composition makes it possible to avoid the abovementioned drawbacks and to improve the cosmetic properties such as smoothness, manageability, disentangling, volume (in particular root lifting), and tonicity of the head of hair.

In particular, the composition according to the invention makes it possible to obtain hair which is smoother, homogeneous and/or more manageable at the time of rinsing. On wet hair, hair is obtained which is easier to disentangle or is more tonic and/or has roots that are more lifted (at the roots, the hair is not plastered against the scalp but forms an angle, which gives volume). In addition, on dry hair, hair is obtained which is more manageable and/or smoother to the touch.

Thus, a subject of the invention is a composition comprising, in an aqueous medium:
from 0.1% to 20% by weight of one or more volatile linear alkanes,
from 0.5% to 25% by weight of one or more silicones having a viscosity of greater than or equal to 20 000 $mm^2/s$ at 25° C.,
one or more non-silicone fatty substances different from the volatile linear alkanes,
the weight ratio of the amount of said non-silicone fatty substance(s) different from the volatile linear alkanes to the amount of said silicone(s) being less than or equal to 5.

The subject of the invention is also the use of said composition for the cosmetic treatment of keratin materials, preferably keratin fibres such as the hair, in particular as a rinse-out hair care product.

Another subject of the invention is a method for cosmetic treatment of keratin materials, preferably keratin fibres such as the hair, using said composition.

The cosmetic composition according to the invention comprises, in an aqueous medium:
from 0.1% to 20% by weight of one or more volatile linear alkanes,
from 0.5% to 25% by weight of one or more silicones having a viscosity of greater than or equal to 20 000 $mm^2/s$,
one or more non-silicone fatty substances different from the volatile linear alkanes,
the weight ratio of the amount of said non-silicone fatty substance(s) different from the volatile linear alkanes to the amount of said silicone(s) being less than or equal to 5, and preferably less than or equal to 3.

Said ratio preferably ranges from 0.01 to 5, more preferentially from 0.1 to 5, and even better still from 0.1 to 3.

The expression "one or more volatile linear alkane(s)" is intended to mean, without distinction, "one or more volatile linear alkane oil(s)".

A volatile linear alkane suitable for the invention is liquid at ambient temperature (approximately 25° C.) and at atmospheric pressure (101 325 Pa or 760 mmHg).

The term "volatile linear alkane" suitable for the invention is intended to mean a linear alkane capable of evaporating on contact with the skin in less than one hour, at ambient temperature (25° C.) and at atmospheric pressure (101 325 Pa), which is liquid at ambient temperature, and which has in particular an evaporation rate ranging from 0.01 to 15 $mg/cm^2/min$, at ambient temperature (25° C.) and at atmospheric pressure (101 325 Pa).

Preferably, the volatile linear alkane(s) suitable for the invention have an evaporation rate ranging from 0.01 to 3.5 $mg/cm^2/min$, better still from 0.01 to 1.5 $mg/cm^2/min$, at ambient temperature (25° C.) and at atmospheric pressure (101 325 Pa).

More preferably, the volatile linear alkane(s) suitable for the invention has (have) an evaporation rate ranging from 0.01 to 0.8 $mg/cm^2/min$, preferentially from 0.01 to 0.3 $mg/cm^2/min$, and even more preferentially from 0.01 to 0.12 $mg/cm^2/min$, at ambient temperature (25° C.) and at atmospheric pressure (101 325 Pa).

The evaporation rate of a volatile alkane in accordance with the invention (and more generally of a volatile solvent) can in particular be evaluated by means of the protocol described in WO 06/013413, and more particularly by means of the protocol described hereinafter.

15 g of volatile hydrocarbon-based solvent are placed in a crystallizing dish (diameter: 7 cm) placed on a balance which is in a chamber of approximately 0.3 $m^3$ with controlled temperature (25° C.) and hygrometry (50% relative humidity).

The volatile hydrocarbon-based solvent is left to evaporate freely, without being stirred, with ventilation being provided by means of a fan (Papst-Motoren, reference 8550 N, operating at 2700 rpm) arranged vertically above the crystallizing dish containing the volatile hydrocarbon-based solvent, the blades being directed towards the crystallizing dish, at a distance of 20 cm relative to the bottom of the crystallizing dish.

The mass of volatile hydrocarbon-based solvent remaining in the crystallizing dish is measured at regular time intervals.

The evaporation profile of the solvent is then obtained by plotting the curve of the amount of product evaporated (in mg/cm$^2$) as a function of time (in min).

The evaporation rate, which corresponds to the tangent at the origin of the curve obtained, is then calculated. The evaporation rates are expressed in mg of volatile solvent evaporated per unit surface area (cm$^2$) and per unit time (minute).

According to one preferred embodiment, the volatile linear alkane(s) suitable for the invention have a non-zero vapour pressure (also known as saturated vapour pressure) at ambient temperature, in particular a vapour pressure ranging from 0.3 Pa to 6000 Pa.

Preferably, the volatile linear alkane(s) suitable for the invention has (have) a vapour pressure ranging from 0.3 to 2000 Pa, better still from 0.3 to 1000 Pa, at ambient temperature (25° C.).

More preferably, the volatile linear alkane(s) suitable for the invention has (have) a vapour pressure ranging from 0.4 to 600 Pa, preferentially from 1 to 200 Pa, and even more preferentially from 3 to 60 Pa, at ambient temperature (25° C.).

According to one embodiment, a volatile linear alkane suitable for the invention can have a flashpoint within the range of from 30 to 120° C., and more particularly from 40 to 100° C. The flashpoint is in particular measured according to standard ISO 3679.

According to one embodiment, the volatile linear alkane(s) suitable in the invention may be a linear alkane or linear alkanes containing from 7 to 15 carbon atoms, preferably from 8 to 14 carbon atoms, and better still from 9 to 14 carbon atoms.

More preferably, the volatile linear alkane(s) suitable in the invention comprise(s) from 10 to 14 carbon atoms, and even more preferentially from 11 to 14 carbon atoms.

The volatile linear alkane(s) suitable for the invention may advantageously be of plant origin.

Preferably, the volatile linear alkane or the mixture of volatile linear alkanes present in the composition according to the invention comprises at least one $^{14}$C isotope of carbon (carbon 14). In particular, the $^{14}$C isotope can be present in a $^{14}$C/$^{12}$C isotope ratio (by number of isotopes) of greater than or equal to $1\times10^{-16}$, preferably greater than or equal to $1\times10^{-15}$, more preferably greater than or equal to $7.5\times10^{-14}$, and better still greater than or equal to $1.5\times10^{-13}$. Preferably, the isotope ratio ranges from $6\times10^{-13}$ to $1.2\times10^{-12}$.

The amount of $^{14}$C isotopes in the volatile linear alkane or the mixture of volatile linear alkanes can be determined by methods known to those skilled in the art, such as the Libby counting method, liquid scintillation spectrometry or accelerator mass spectrometry.

Such an alkane or mixture of alkanes can be obtained, directly or in several steps, from a plant starting material such as an oil, a butter, a wax, etc.

By way of examples of alkanes suitable for the invention, mention may be made of the alkanes described in patent applications WO 2007/068371 and WO 2008/155059. These alkanes are obtained from fatty alcohols, which are themselves obtained from coconut oil or from palm oil.

By way of examples of linear alkanes suitable for the invention, mention may be made of n-heptane (C7), n-octane (C8), n-nonane (C9), n-decane (C10), n-undecane (C11), n-dodecane (C12), n-tridecane (C13), n-tetradecane (C14), and mixtures thereof. According to one particular embodiment, the volatile linear alkane is chosen from n-nonane, n-undecane, n-dodecane, n-tridecane and n-tetradecane, and mixtures thereof.

According to one preferred embodiment, mention may be made of the mixtures of n-undecane (C11) and n-tridecane (C13) obtained in particular in Examples 1 and 2 of application WO 2008/155059.

Mention may also be made of n-dodecane (C12) and n-tetradecane (C14) sold, respectively, under the references Parafol 12-97 and Parafol 14-97 by the company Sasol, and also mixtures thereof.

One embodiment consists in using a single volatile linear alkane.

Alternatively, use may be made of a mixture of at least two different volatile linear alkanes which differ from one another in the number of carbons n by at least 1, in particular which differ from one another in the number of carbons by 1 or 2.

According to one embodiment, use is made of a mixture of at least two different volatile linear alkanes containing from 10 to 14 carbon atoms and which differ from one another in the number of carbons by at least 1. By way of examples, mention may in particular be made of C10/C11, C11/C12 or C12/C13 volatile linear alkane mixtures.

According to another embodiment, use is made of a mixture of at least two separate volatile linear alkanes containing from 10 to 14 carbon atoms and which differ from one another in the number of carbons by at least 2. By way of examples, mention may in particular be made of C10/C12 or C12/C14 volatile linear alkane mixtures, for an even number of carbons n, and the C11/C13 mixture for an odd number of carbons n.

According to one preferred embodiment, use is made of a mixture of at least two different volatile linear alkanes containing from 10 to 14 carbon atoms and which differ from one another in the number of carbons by at least 2, and in particular a C11/C13 volatile linear alkane mixture or a C12/C14 volatile linear alkane mixture.

Other mixtures combining more than 2 volatile linear alkanes according to the invention, for instance a mixture of at least 3 different volatile linear alkanes containing from 7 to 15 carbon atoms and which differ from one another in the number of carbons by at least 1, can be used in the invention.

In the case of the mixtures of two volatile linear alkanes, said two volatile linear alkanes preferably represent more than 95%, and better still more than 99% by weight of the mixture.

According to one particular embodiment of the invention, in a mixture of volatile linear alkanes, the volatile linear alkane having the lowest carbon number is predominant in the mixture.

According to another embodiment of the invention, use is made of a mixture of volatile linear alkanes in which the volatile linear alkane having the highest carbon number is predominant in the mixture.

By way of examples of mixtures suitable for the invention, mention may in particular be made of the following mixtures:
from 50% to 90% by weight, preferably from 55% to 80% by weight, more preferentially from 60% to 75% by weight of C$_n$ volatile linear alkane with n ranging from 7 to 15,
from 10% to 50% by weight, preferably from 20% to 45% by weight, preferably from 24% to 40% by weight of C$_{n+x}$ volatile linear alkane with x greater than or equal to 1, preferably x=1 or x=2, with n+x between 8 and 14, relative to the total weight of the alkanes in said mixture.

In particular, said mixture of volatile linear alkanes can also contain:
- less than 2% by weight, preferably less than 1% by weight of branched hydrocarbons,
- and/or less than 2% by weight, preferably less than 1% by weight of aromatic hydrocarbons,
- and/or less than 2% by weight, preferably less than 1% by weight and preferentially less than 0.1% by weight of unsaturated hydrocarbons, said percentages being expressed relative to the total weight of the mixture.

More particularly, the volatile linear alkanes suitable in the invention can be used in the form of an n-undecane/n-tridecane mixture.

In particular, use will be made of a mixture of volatile linear alkanes comprising:
- from 55% to 80% by weight, preferably from 60% to 75% by weight, of C11 volatile linear alkane (n-undecane) and
- from 20% to 45% by weight, preferably from 24% to 40% by weight, of C13 volatile linear alkane (n-tridecane), relative to the total weight of the alkanes in said mixture.

According to one particular embodiment, the mixture of alkanes is an n-undecane/n-tridecane mixture. In particular, such a mixture can be obtained according to Example 1 or Example 2 of application WO 2008/155059.

According to another particular embodiment, the n-dodecane sold under the reference Parafol 12-97 by Sasol is used.

According to another particular embodiment, the n-tetradecane sold under the reference Parafol 14-97 by Sasol is used.

According to yet another embodiment, a mixture of n-dodecane and n-tetradecane, preferably in an 85/15 ratio, such as the mixture sold under the name Vegelight 1214 by the company Biosynthis, is used.

The composition of the invention preferably comprises from 1% to 20% by weight of volatile linear alkane(s), in particular from 1% to 15% by weight, and more particularly from 3% to 15% by weight of volatile linear alkane(s), relative to the total weight of the composition.

In the interest of simplicity, the kinematic viscosity of the compound is denoted "viscosity".

The silicone(s) that can be used in accordance with the present invention has (have) a viscosity of greater than or equal to 20 000 mm$^2$/s, preferably greater than or equal to 50 000 mm$^2$/s, and even better still greater than or equal to 100 000 mm$^2$/s. In general, they have a viscosity of less than 200 000 000 mm$^2$/s.

More preferably, the silicone(s) is (are) chosen from silicones having a viscosity ranging from 100 000 to 150 000 000 mm$^2$/s, preferably ranging from 1 000 000 to 50 000 000 mm$^2$/s.

The viscosity of the silicone is preferably measured using a Poiseuille rheometer, at a temperature of 25° C., according to standard ASTM-D445-97. The "falling ball" method can also be used. When the silicone is used as a mixture in a solvent or in the form of an emulsion, the viscosity of the silicone alone is measured, independently of the mixture solvent.

The silicone(s) that can be used in the composition according to the invention is (are) in particular polyorganosiloxanes which can be in the form of aqueous solutions, i.e. solubilized, or optionally in the form of dispersions or microdispersions, or of aqueous emulsions. The polyorganosiloxanes can also be in the form of oils, waxes, resins or gums.

The organopolysiloxanes are defined in greater detail in the book by Walter Noll "Chemistry and Technology of Silicones" (1968) Academic Press. In the context of the present invention, the expression "silicone having a viscosity of greater than or equal to 20 000 mm$^2$/s" is intended to mean:

(i) polyalkylsiloxanes; among polyalkylsiloxanes, mention may mainly be made of linear polydimethylsiloxanes with trimethylsilyl end groups, and polydimethylsiloxanes with hydroxydimethysilyl end groups for instance;

(ii) polyarylsiloxanes;

(iii) polyalkylarylsiloxanes; mention may be made of linear and branched polymethylphenylsiloxanes, polydimethylmethylphenylsiloxanes and polydimethyldiphenylsiloxanes,
and in particular, (iv) silicone gums, such as the gums of the silicones (i), (ii) and (iii); these are polydiorganosiloxanes with a molecular mass of between 200 000 and 5 000 000, used alone or as a mixture in a solvent chosen from volatile silicones, polydimethylsiloxane (PDMS) oils, polyphenylmethylsiloxane (PPMS) oils, isoparaffins, methylene chloride, pentane or mixtures thereof; they can, for example, have one of the following structures:
- polydimethylsiloxane,
- poly[(dimethylsiloxane)/(methylvinylsiloxane)],
- poly[(dimethylsiloxane)/(vinylhydrogenosiloxane)],
- poly[(dihydrogenodimethylsiloxane)/(divinylsiloxane)],
- poly[(dimethylsiloxane)/(diphenylsiloxane)],
- poly[(dimethylsiloxane)/(phenylmethylsiloxane)],
- poly[(dimethylsiloxane)/(diphenylsiloxane)/(methylvinylsiloxane)];

mention may also be made, for example, and in a nonlimiting manner, of the following mixtures:

1) mixtures formed from a polydimethylsiloxane hydroxylated at the end of a chain (Dimethiconol according to the CTFA nomenclature), and from a cyclic polydimethylsiloxane (Cyclomethicone according to the CTFA nomenclature), such as the product Q2 1401 sold by the company Dow Corning;

2) mixtures formed from a polydimethylsiloxane gum with a cyclic silicone, such as the product SF 1214 Silicone Fluid from General Electric, which is an SE 30 gum of MW 500 000 dissolved in SF 1202 Silicone Fluid (decamethyl cyclopentasiloxane);

3) mixtures of two PDMSs of different viscosity, in particular of a PDMS gum and of a PDMS oil, such as the products SF 1236 and CF 1241 from the company General Electric;

(v) silicone resins; preferably crosslinked siloxane systems containing $RSiO_{2/2}$, $RSiO_{3/2}$ and $SiO_{4/2}$ units in which R represents a hydrocarbon-based group containing 1 to 6 carbon atoms or a phenyl group. Among these resins, mention may be made of the product sold under the name Dow Corning 593;

(vi) or mixtures thereof.

These silicones can be used as they are or in the form of solutions in organic solvents or else in the form of emulsions or microemulsions.

Preferably, the silicone is in the form of an aqueous emulsion.

The term "aqueous emulsion" is intended to mean an emulsion of oil-in-water type in which the silicone copolymer is dispersed in the form of particles or droplets in the aqueous phase forming the continuous phase of the emulsion.

This emulsion can be stabilized with a customary emulsifying system.

This silicone emulsion can have a silicone droplet or particle size ranging from 10 nm to 50 μm, and preferably from 0.3 μm to 20 μm.

The particle size is measured by laser particle sizing.

The emulsifying system comprises surfactants that are normally used in silicone emulsions. These surfactants may be non-ionic, cationic, anionic or amphoteric surfactants or mixture thereof.

The emulsifying system preferably represents from 0.5% to 10% by weight, relative to the total weight of the emulsion.

The preferred polyorganosiloxane(s) that can be used according to the invention is (are) in particular the product(s) belonging to class (i) and in particular to subclass (iv).

In one preferred embodiment, the silicone(s) that can be used according to the invention is (are) chosen from the silicone gums as described above, and more preferably those which have a poly[(dihydrogenodimethylsiloxane)/(divinylsiloxane)] structure.

Such emulsions are in particular sold under the name DC2-1997 cationic emulsion by the company Dow Corning. This emulsion comprises an alpha, omega-vinyl dimethicone/alpha, omega-hydrogen dimethicone copolymer which has a kinematic viscosity of approximately $20 \times 10^6$ cSt (centistokes), a cationic emulsifier such as cetyltrimethylammonium chloride, a stabilizer of hydroxyethylcellulose type, and water.

The silicone(s) having a viscosity of greater than or equal to 20 000 $mm^2/s$ is (are) preferably present in proportions ranging from 0.1% to 10% by weight, relative to the total weight of the composition, and preferentially from 0.5% to 5% by weight, relative to the total weight of the composition.

As explained previously, the composition according to the invention also comprises one or more non-silicone fatty substances. The non-silicone fatty substances used in the invention are different from the volatile linear alkanes previously defined.

The term "fatty substance" is intended to mean an organic compound which is insoluble in water at ordinary temperature (25° C.) and at atmospheric pressure (760 mmHg), i.e. which has a solubility of less than 5%, and preferably less than 1%, even more preferentially less than 0.1%. The non-silicone fatty substances have, in their structure, a hydrocarbon-based chain containing at least 6 carbon atoms and not comprising a siloxane group. In addition, the fatty substances are generally soluble in organic solvents under the same temperature and pressure conditions, for example chloroform, ethanol, benzene, liquid petroleum jelly or decamethylcyclopentasiloxane.

Preferably, the non-silicone fatty substance(s) is (are) chosen from $C_8$-$C_{40}$ fatty alcohols, esters of a $C_8$-$C_{40}$ fatty acid and/or of a $C_8$-$C_{40}$ fatty alcohol, waxes, and plant, animal, mineral and synthetic oils, which are different from the volatile linear alkanes as defined above.

The $C_8$-$C_{40}$ fatty alcohol(s) can be chosen from alcohols of formula R'OH, where R' denotes a linear or branched, saturated or unsaturated radical containing from 8 to 40 carbon atoms, preferably 8 to 30 carbon atoms. R' preferably denotes a $C_{12}$-$C_{24}$ alkyl or $C_{12}$-$C_{14}$ alkenyl group. R' can be substituted with one or more hydroxyl groups.

The fatty alcohol(s) may in particular be chosen from lauryl alcohol, hexyldecanol, 2-octyldodecanol, cetyl alcohol, dodecyl alcohol, decyl alcohol, stearyl alcohol, oleyl alcohol, behenyl alcohol, linoleyl alcohol, undecylenyl alcohol, palmitoleyl alcohol, arachidonyl alcohol, myristyl alcohol and erucyl alcohol. A mixture of fatty alcohols may also be used, which means that several species of fatty alcohols may coexist in a commercial product, in the form of a mixture. By way of a mixture of fatty alcohols, mention may be made of cetylstearyl alcohol or cetearyl alcohol.

More preferably, the fatty alcohol(s) is (are) chosen from lauryl alcohol, myristyl alcohol, cetyl alcohol, stearyl alcohol, cetylstearyl alcohol, oleyl alcohol, behenyl alcohol, hexyldecanol, 2-octyldodecanol, and mixtures thereof.

The esters of a $C_8$-$C_{40}$ fatty acid and/or of a $C_8$-$C_{40}$ fatty alcohol can in particular be mono-, di- or polyesters of a $C_8$-$C_{40}$ fatty acid and/or of a $C_8$-$C_{40}$ fatty alcohol. Among these, monoesters of a $C_8$-$C_{40}$ fatty alcohol as defined above and/or of a $C_8$-$C_{40}$ fatty acid as defined below are preferably used.

The $C_8$-$C_{40}$ fatty acids can be chosen from acids of formula RCOOH, where R is a linear or branched, saturated or unsaturated radical containing from 7 to 39 carbon atoms. Preferably, R is a $C_7$-$C_{29}$ alkyl or $C_7$-$C_{29}$ alkenyl group, better still a $C_{12}$-$C_{24}$ alkyl or $C_{12}$-$C_{24}$ alkenyl group. R can be substituted with one or more hydroxyl groups and/or one or more carboxyl groups. The fatty acid can in particular be chosen from lauric acid, oleic acid, palmitic acid, linoleic acid, myristic acid and stearic acid.

Waxes are natural (animal or plant) or synthetic substances which are solid in ambient temperature (20°-25° C.). They are insoluble in water and soluble in oils and are capable of forming a water-repellent film.

As regards the definition of waxes, mention may, for example, be made of P. D. Dorgan, Drug and Cosmetic Industry, December 1983, pp. 30-33.

The wax(es) optionally present in the composition according to the invention can be chosen in particular from carnauba wax, candelilla wax, esparto grass wax, paraffin wax, ozokerite, plant waxes such as olive wax, rice wax, hydrogenated jojoba wax or the absolute waxes of flowers, such as the essential wax of blackcurrant blossom, animal waxes, for instance beeswaxes or modified beeswaxes (cerabellina); other waxes or waxy starting materials that can be used according to the invention are in particular marine waxes such as the product sold by the company Sophim under the reference M82, and polyethylene waxes or polyolefin waxes.

By way of oils that can be used in the composition of the invention and that are different from the volatile linear alkanes, mention may, for example, be made of:

branched hydrocarbon-based oils of animal origin, such as perhydrosqualene;

hydrocarbon-based oils of plant origin, such as liquid fatty acid triglycerides containing from 4 to 10 carbon atoms, for instance heptanoic or octanoic acid triglycerides, or alternatively, for example, jojoba oil, avocado oil, rapeseed oil, olive oil, sunflower oil, maize oil, soybean oil, marrow oil, grapeseed oil, sesame oil, hazelnut oil, apricot oil, macadamia oil, arara oil, castor oil, caprylic/capric acid triglycerides such as those sold by the company Stearineries Dubois or those sold under the names Miglyol® 810, 812 and 818 by the company Dynamit Nobel, jojoba oil and shea butter oil;

branched hydrocarbons of mineral or synthetic origin, such as volatile or non-volatile liquid paraffins, and derivatives thereof, petroleum jelly, hydrogenated polyisobutene such as Parléam®; and isoparaffins for instance isohexadecane and isodecane;

fluoro oils with partial hydrocarbon modification; as fluoro oils, mention may also be made of perfluoromethylcyclopentane and perfluoro-1,3 dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or else bromoperfluorooctyl sold under the name Foralkyl® by the company Atochem; nonafluoromethoxybutane and nonafluoroethoxyisobutane; perfluoromorpholine derivatives, such as 4-trifluoromethyl perfluoromorpholine sold under the name PF 5052® by the company 3M.

Preferably, the fatty substance(s) does (do) not comprise an oxyalkylenated unit, nor a glycerolated unit.

Among all the fatty substances that can be used according to the invention, the fatty substance(s) are preferably chosen from the fatty alcohols mentioned above and the waxes as defined above.

The non-silicone fatty substance(s) different from the volatile linear alkanes represent(s) from 0.5% to 25%, preferably from 1% to 10%, by weight, of the total weight of the composition.

The composition according to the invention can also comprise one or more cationic polymers.

For the purpose of the present invention, the term "cationic polymer" is intended to mean any polymer comprising cationic groups and/or groups that can be ionized to cationic groups.

The cationic polymer(s) that can be used in the cosmetic composition according to the invention is (are) preferably chosen from polymers comprising primary, secondary, tertiary and/or quaternary amine groups which are part of the polymer chain or directly connected thereto, and which have a number-average molecular mass of between 500 and approximately 5 000 000, and preferably between 1000 and 3 000 000.

Among these polymers, mention may more particularly be made of the following cationic polymers:

(1) homopolymers or copolymers of acrylic or methacrylic esters or amides with amine functions, comprising at least one of the units having the following formulae:

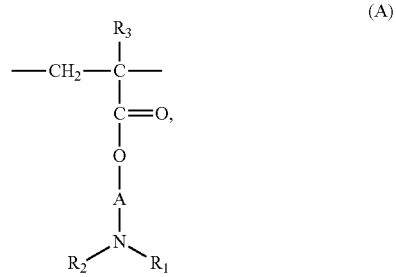

(A)

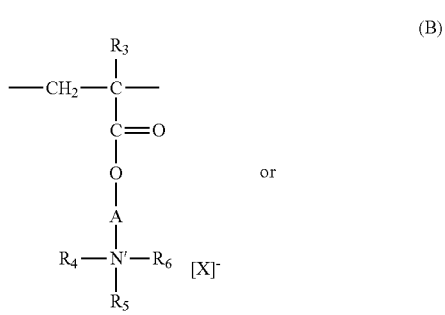

(B)

or

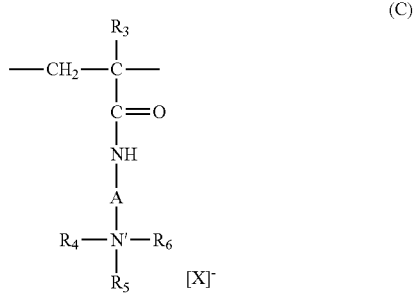

(C)

in which:

$R_1$ and $R_2$, which may be identical or different, each represent a hydrogen atom or an alkyl group having from 1 to 6 carbon atoms;

$R_3$ denotes a hydrogen atom or a $CH_3$ group;

A is a linear or branched alkyl group containing from 1 to 6 carbon atoms or a hydroxyalkyl group containing from 1 to 4 carbon atoms;

$R_4$, $R_5$ and $R_6$, which may be identical or different, represent an alkyl group having from 1 to 18 carbon atoms or a benzyl group;

$X^-$ denotes a methosulphate anion or a halide such as chloride or bromide. The copolymers of family (1) also contain one or more units deriving from comonomers that may be chosen from the family of acrylamides, methacrylamides, diacetone acrylamides, acrylamides and methacrylamides substituted on the nitrogen with lower ($C_{1-4}$) alkyl groups, groups derived from acrylic or methacrylic acids or esters thereof, vinyllactams such as vinylpyrrolidone or vinylcaprolactam, and vinyl esters.

Thus, among these copolymers of family (1), mention may be made of:

copolymers of acrylamide and of dimethylaminoethyl methacrylate quaternized with dimethyl sulphate or with a dimethyl halide, such as the product sold under the name Hercofloc® by the company Hercules, copolymers of acrylamide and of methacryloyloxyethyltrimethylammonium chloride, described, for example, in Patent Application EP-A-080976 and sold under the name Bina Quat P 100 by the company Ciba Geigy, copolymers of acrylamide and of methacryloyloxyethyltrimethylammonium methosulphate, such as the product sold under the name Reten by the company Hercules, quaternized or non-quaternized vinylpyrrolidone/dialkylaminoalkyl acrylate or methacrylate copolymers, such as the products sold under the name Gafquat® by the company ISP, for instance Gafquat® 734 or Gafquat® 755, or else the products known as Copolymer® 845, 958 and 937. These polymers are described in detail in French Patents Nos 2 077 143 and 2 393 573, dimethylaminoethyl methacrylate/vinylcaprolactam/vinylpyrrolidone terpolymers, such as the product sold under the name Gaffix® VC 713 by the company ISP, and quaternized vinylpyrrolidone/dimethylaminopropylmethacrylamide copolymers, such as in particular the product sold under the name Gafquat® HS 100 by the company ISP;

crosslinked polymers of methacryloyloxy($C_1$-$C_4$)alkyltri ($C_1$-$C_4$)alkylammonium salts, such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with an olefinically unsaturated compound, in particular methylenebisacrylamide. Use may more particularly be made of a crosslinked acrylamide/methacryloyloxyethyltrimethylammonium chloride copolymer (20/80 by weight) in the form of a dispersion containing 50% by weight of said copolymer in mineral oil. This dispersion is sold under the name Salcare® SC 92 by the company Ciba. Use may also be made of a crosslinked methacryloyloxyethyl-trimethylammonium chloride homopolymer containing approximately 50% by weight of the homopolymer in mineral oil or in a liquid ester. These dispersions are sold under the names Salcare® SC 95 and Salcare® SC 96 by the company Ciba;

(2) cationic polysaccharides, in particular those chosen from:

a) cellulose ether derivatives comprising quaternary ammonium groups, described in Patent FR 1492597. These polymers are also defined in the CTFA dictionary as quaternary ammoniums of hydroxyethylcellulose that has reacted with an epoxide substituted with a trimethylammonium group;

b) cellulose derivatives grafted with a water-soluble monomer comprising a quaternary ammonium, and described in particular in U.S. Pat. No. 4,131,576, such as hydroxyalkylcelluloses, for instance hydroxymethyl, hydroxyethyl or hydroxypropyl celluloses grafted in particular with a methacryloyloxyethyltrimethylammonium, methacrylamidopropyltrimethylammonium or dimethyldiallylammonium salt.

The commercial products corresponding to this definition are more particularly the products sold under the name Celquat L 200 and Celquat H 100 by the company National Starch;

c) cationic polygalactomanans such as those described in U.S. Pat. Nos. 3,589,578 and 4,031,307, such as guar gums containing cationic trialkylammonium groups. Such products are sold in particular under the trade names Jaguar C13 S, Jaguar C 15 and Jaguar C 17 by the company Meyhall;

(3) quaternary copolymers of vinylpyrrolidone and of vinylimidazole;

(4) chitosans or salts thereof; the salts that can be used are in particular chitosan acetate, lactate, glutamate, gluconate or pyrrolidonecarboxylate.

Among these compounds, mention may be made of chitosan having a degree of deacetylation of 90.5% by weight, sold under the name Kytan Brut Standard by the company Aber Technologies, and chitosan pyrrolidonecarboxylate, sold under the name Kytamer® PC by the company Amerchol.

Among all the cationic polymers that may be present in the composition according to the invention, the cationic polymer(s) are preferably chosen from crosslinked polymers of methacryloyloxy($C_1$-$C_4$)alkyltri($C_1$-$C_4$)alkylammonium salts, and cationic polysaccharides.

When the composition comprises at least one cationic polymer, this or these polymer(s) is (are) present in a concentration preferably ranging from 0.01% to 10% by weight, relative to the total weight of the composition.

The composition according to the invention may also comprise one or more surfactants chosen from anionic, cationic, non-ionic or amphoteric surfactants.

Preferably, the surfactant(s) is (are) cationic.

The term "cationic surfactant" is intended to mean a surfactant which is positively charged when it is contained in the composition according to the invention. This surfactant may carry one or more charges that are permanently positive or contain one or more functions which are cationizable in the composition according to the invention. By way of example of cationic surfactants that can be used in the cosmetic composition, mention may in particular be made of primary, secondary or tertiary fatty amines, which are optionally polyoxyalkylenated, or salts thereof, quaternary ammonium salts, and mixtures thereof.

The fatty amines generally comprise at least one $C_8$-$C_{30}$ hydrocarbon-based chain. Among the fatty amines that can be used according to the invention, mention may be made, for example, of stearylamidopropyldimethylamine.

The fatty amines generally comprise at least one $C_8$-$C_{30}$ hydrocarbon-based chain. Among the fatty amines that can be used according to the invention, mention may, for example, be made of stearylamidopropyldimethylamine and distearylamine.

By way of quaternary ammonium salts, mention may in particular be made, for example, of:

those which have general formula (I) below:

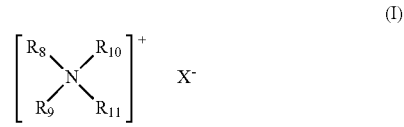

in which the radicals $R_8$ to $R_{11}$, which may be identical or different, represent a linear or branched aliphatic radical containing from 1 to 30 carbon atoms, or an aromatic radical such as an aryl or alkylaryl radical, at least one of the radicals $R_8$ to $R_{11}$ containing from 8 to 30 carbon atoms, preferably from 12 to 24 carbon atoms. The aliphatic radicals may comprise heteroatoms such as, in particular, oxygen, nitrogen, sulphur and halogens.

The aliphatic radicals are, for example, chosen from alkyl, alkoxy, polyoxy($C_2$-$C_6$)alkylene, alkylamide, ($C_{12}$-$C_{22}$)alkylamido($C_2$-$C_6$)alkyl, ($C_{12}$-$C_{12}$)alkyl acetate and hydroxyalkyl radicals, containing approximately from 1 to 30 carbon atoms; $X^-$ is an anion chosen from the group of halides, phosphates, acetates, lactates, ($C_2$-$C_6$)alkyl sulphates, alkyl sulphonates or alkylaryl sulphonates;

quaternary ammonium salts of imidazoline, for instance those of formula (II) below:

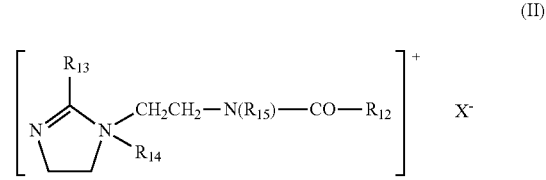

in which $R_{12}$ represents an alkenyl or alkyl radical containing from 8 to 30 carbon atoms, for example fatty acid derivatives of tallow, $R_{13}$ represents a hydrogen atom, a $C_1$-$C_4$ alkyl radical or an alkenyl or alkyl radical containing from 8 to 30 carbon atoms, $R_{14}$ represents a $C_1$-$C_4$ alkyl radical, $R_{15}$ represents a hydrogen atom or a $C_1$-$C_4$ alkyl radical, and $X^-$ is an anion chosen from the group of halides, phosphates, acetates, lactates, alkyl sulphates, alkyl sulphonates or alkylaryl sulphonates. Preferably, $R^{12}$ and $R_{13}$ denote a mixture of alkenyl or alkyl radicals containing from 12 to 21 carbon atoms, for example fatty acid derivatives of tallow, $R_{14}$ denotes a methyl radical, and $R_{15}$ denotes a hydrogen atom. Such a product is, for example, sold under the name Rewoquat® W 75 by the company Rewo;

diquaternary ammonium salts of formula (III):

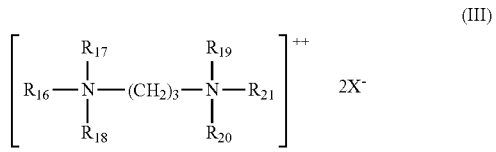

in which $R_{16}$ denotes an aliphatic radical containing approximately from 16 to 30 carbon atoms, $R_{17}$, $R_{18}$, $R_{19}$, $R_{20}$ and $R_{21}$, which may be identical or different, are chosen from hydrogen or an alkyl radical containing from 1 to 4 carbon atoms, and $X^-$ is an anion chosen from the group of halogens, acetates, phosphates, nitrates and methyl sulphates. Such diquaternary ammonium salts in particular comprise propanetallowediammonium dichloride;

quaternary ammonium salts containing at least one ester function, such as those of formula (IV) below:

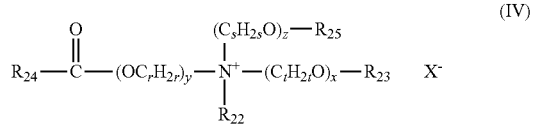

in which:

$R_{22}$ is chosen from $C_1$-$C_6$ alkyl radicals and $C_1$-$C_6$ hydroxyalkyl or dihydroxyalkyl radicals;

$R_{23}$ is chosen from:

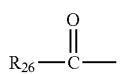

the radical linear or branched, saturated or unsaturated $C_1$-$C_{22}$ hydrocarbon-based radicals $R_{27}$, a hydrogen atom, $R_{25}$ is chosen from:

the radical

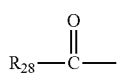

linear or branched, saturated or unsaturated $C_1$-$C_6$ hydrocarbon-based radicals $R_{29}$, a hydrogen atom, $R_{24}$, $R_{26}$ and $R_{28}$, which may be identical or different, are chosen from linear or branched, saturated or unsaturated $C_7$-$C_{21}$ hydrocarbon-based radicals;

r, s and t, which may be identical or different, are integers ranging from 2 to 6;

y is an integer ranging from 1 to 10;

x and z, which may be identical or different, are integers ranging from 0 to 10;

$X^-$ is a simple or complex, organic or inorganic anion;

with the proviso that the sum x+y+z is from 1 to 15, that when x is 0, then $R_{23}$ denotes $R_{27}$ and that when z is 0, then $R_{25}$ denotes $R_{29}$.

The alkyl radicals $R^{22}$ may be linear or branched, and more particularly linear.

Preferably, $R_{22}$ denotes a methyl, ethyl, hydroxyethyl or dihydroxypropyl radical, and more particularly a methyl or ethyl radical.

Advantageously, the sum x+y+z is from 1 to 10.

When $R_{23}$ is a hydrocarbon-based radical $R_{27}$, it may be long and contain from 12 to 24 carbon atoms, or short and contain from 1 to 3 carbon atoms.

When $R_{25}$ is a hydrocarbon-based radical $R_{29}$, it preferably contains 1 to 3 carbon atoms.

Advantageously, $R_{24}$, $R_{26}$ and $R_{28}$, which may be identical or different, are chosen from linear or branched, saturated or unsaturated $C_{11}$-$C_{21}$ hydrocarbon-based radicals, and more particularly from linear or branched, saturated or unsaturated $C_{11}$-$C_{21}$ alkyl and alkenyl radicals.

Preferably, x and z, which may be identical or different, are equal to 0 or 1.

Advantageously, y is equal to 1.

Preferably, r, s and t, which may be identical or different, are equal to 2 or 3, and even more particularly are equal to 2.

The anion $X^-$ is preferably a halide (chloride, bromide or iodide) or an alkyl sulphate, more particularly methyl sulphate. However, methanesulphonate, phosphate, nitrate, tosylate, an anion derived from an organic acid, such as acetate or lactate, or any other anion that is compatible with the ammonium containing an ester function, may be used.

The anion $X^-$ is even more particularly chloride or methyl sulphate.

Use is made more particularly, in the composition according to the invention, of the ammonium salts of formula (IV) in which:

$R_{22}$ denotes a methyl or ethyl radical;

x and y are equal to 1;

z is equal to 0 or 1;

r, s and t are equal to 2;

$R_{23}$ is chosen from:

the radical

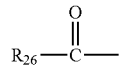

methyl, ethyl or $C_{14}$-$C_{22}$ hydrocarbon-based radicals, a hydrogen atom;

$R_{25}$ is chosen from:

the radical

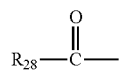

a hydrogen atom;

$R_{24}$, $R_{26}$ and $R_{28}$, which may be identical or different, are chosen from linear or branched, saturated or unsaturated $C_{13}$-$C_{17}$ hydrocarbon-based radicals, and preferably from linear or branched, saturated or unsaturated $C_{13}$-$C_{17}$ alkyl and alkenyl radicals.

Advantageously, the hydrocarbon-based radicals are linear.

Mention may be made, for example, of the compounds of formula (IV) such as the diacyloxyethyldimethylammonium, diacyloxyethylhydroxyethylmethylammonium, monoacyloxyethyldihydroxy-ethylmethylammonium, triacyloxyethylmethylammonium and monoacyloxyethylhydroxyethyldimethylammonium salts (chloride or methyl sulphate in particular), and mixtures thereof. The acyl radicals preferably contain 14 to 18 carbon atoms and are obtained more particularly from a plant oil such as palm oil or sunflower oil. When the compound contains several acyl radicals, these radicals may be identical or different.

These products are obtained, for example, by direct esterification of triethanolamine, of triisopropanolamine, of an alkyldiethanolamine or of an alkyldiisopropanolamine, which are optionally oxyalkylenated, with fatty acids or with mixtures of fatty acids of plant or animal origin, or by trans-esterification of the methyl esters thereof. This esterification is followed by a quaternization using an alkylating agent such as an alkyl halide (preferably a methyl or ethyl halide), a dialkyl sulphate (preferably a dimethyl or diethyl sulphate), methyl methanesulphonate, methyl para-toluenesulphonate, and glycol chlorohydrin or glycerol chlorohydrin.

Such compounds are sold, for example, under the names Dehyquart® by the company Henkel, Stepanquat® by the company Stepan, Noxamium® by the company CECA, Rewoquat®WE 18 by the company Rewo-Witco.

The composition according to the invention preferably contains a mixture of quaternary ammonium mono-, di- and triester salts, with a weight majority of diester salts.

As mixture of ammonium salts, use may, for example, be made of the mixture containing 15% to 30% by weight of acyloxyethyldihydroxyethylmethylammonium methyl sulphate, 45% to 60% of diacyloxyethylhydroxyethylmethylammonium methyl sulphate and 15% to 30% of triacyloxyethylmethylammonium methyl sulphate, the acyl radicals containing from 14 to 18 carbon atoms and being obtained from palm oil which is optionally partially hydrogenated.

It is also possible to use the ammonium salts containing at least one ester function that are described in U.S. Pat. No. 4,874,554 and U.S. Pat. No. 4,137,180.

Among the quaternary ammonium salts of formula (I) those preferably used are, on the one hand, tetraalkylammonium chlorides, for instance dialkyldimethylammonium chlorides or alkyltrimethylammonium chlorides in which the alkyl radical contains approximately from 12 to 22 carbon atoms, in particular behenyltrimethylammonium chloride, distearyldimethylammonium chloride, cetyltrimethylammonium chloride, or benzyldimethylstearylammonium chloride, or, on the other hand, distearoylethylhydroxyethylmethylammonium methosulphate, dipalmitoylethylhydroxyethylammonium methosulphate or dicetylaroylethylhydroxyethylammonium methosulphate, or alternatively, finally, palmitylamidopropyltrimethylammonium chloride or stearamidopropyldimethyl(myristyl acetate)ammonium chloride sold under the name Ceraphyl® 70 by the company Van Dyk.

Among all the cationic surfactants that may be present in the composition according to the invention, the cationic surfactant(s) is (are) preferably chosen from cetyltrimethylammonium (INCI: cetrimonium-), behenyltrimethylammonium (INCI: behentrimonium-), dipalmitoylethylhydroxyethylammonium, distearoylethylhydroxyethylmethylammonium, methyl($C_9$-$C_{19}$)alkyl($C_{10}$-$C_{20}$)alkylamidoethylimidazolium and stearamidopropyldimethylamine salts (chloride or methosulphate), and the stearamidopropyldimethylammonium salt, and mixtures thereof.

When the composition comprises at least one cationic surfactant, this or these surfactant(s) is (are) present in a concentration preferably ranging from 0.1% to 10% by weight, relative to the total weight of the composition.

The composition according to the invention comprises an aqueous medium.

The aqueous medium is made up of water or of a mixture of water and at least one cosmetically acceptable solvent, preferably chosen from $C_1$-$C_4$ lower alcohols, such as ethanol, isopropanol, tert-butanol or n-butanol; polyols such as glycerol, propylene glycol and polyethylene glycols; and mixtures thereof. When the medium comprises at least one solvent, it comprises predominantly water, i.e. at least 50% by weight of water relative to the total weight of the aqueous medium.

The composition according to the invention may also comprise one or more conventional additives well known in the art, which are different from the compounds defined above. By way of examples of additives that can be used according to the invention, mention may be made of ionic or non-ionic, associative or non-associative polymers, screens, silanes, silicones having a viscosity of less than 20 000 $mm^2$/s, polyols, proteins, vitamins, reducing agents, plasticizers, emollients, antifoams, moisturizers, pigments, clays, mineral fillers, UV-screening agents, mineral colloids, peptizers, solubilizers, fragrances, preservatives, pearlescent agents, propellants, and inorganic or organic thickeners; these additives being different from the compounds defined above.

Those skilled in the art will take care to select the optional additive(s) and the amount thereof in such a way that they do not harm the properties of the compositions of the present invention.

The additive(s) is (are) generally present in the composition according to the invention in an amount ranging from 0 to 20% by weight, relative to the total weight of the composition.

The compositions according to the invention may be in the form of rinse-out or leave-in care compositions, these compositions being in the form of a more or less thickened lotion, a cream, a gel or an emulsion.

Another subject of the invention is the use of the cosmetic composition as described above, for the cosmetic treatment of keratin materials, preferably keratin fibres such as the hair, and in particular as a rinse-out hair product.

The invention also relates to a method for cosmetic treatment of keratin materials, preferably keratin fibres such as the hair, which comprises applying an effective amount of a cosmetic composition as described above to said materials and, optionally, rinsing out said composition after an optional leave-on time.

When the composition according to the invention is applied in the form of a lotion or a cream, it is optionally left on the hair for approximately 0.5 to 5 minutes, and then optionally rinsed out with water.

The following examples are given by way of illustration of the present invention.

In the following examples, all the amounts are indicated as percentage by weight of product as it is, relative to the total weight of the composition, unless otherwise indicated.

EXAMPLES

The following rinse-out care compositions A, B and C were prepared from the ingredients indicated in the table below.

|  | Compositions | | |
| --- | --- | --- | --- |
|  | A | B | C |
| Mixture of n-undecane and n-tridecane according to Example 2 of WO 2008/155059 | 5 | 3 | — |
| Mixture of dodecane and tetradecane, pure (85/15), sold under the trade name Vegelight by Biosynthis | — | — | 5 |
| Copolymer of polydimethylsiloxane containing alpha, omega-vinyl/alpha, omega-hydrogen polysiloxane groups in a cationic emulsion, sold under the trade name Dow Corning 2-1997 by the company Dow Corning (viscosity of approximately $20 \times 10^6$ mm$^2$/s) 67% by weight of active material | 2 | 2 | 2 |
| Myristyl alcohol, sold under the trade name Nacol 14-98 by the company Sasol | 3 | 3 | 3 |
| Cetyl alcohol, sold under the trade name Nacol 16-98 by the company Sasol | 1 | 1 | 1 |
| Crosslinked ethyltrimethylammonium methacrylate chloride homopolymer, as an inverse emulsion at 50% by weight in a mineral oil, sold under the trade name Salcare ® SC 95 by the company Ciba | 0.5 | 0.5 | 0.5 |
| Stearylamidopropyldimethylamine, sold under the trade name Mackine 301 by the company Rhodia | 2.5 | 2.5 | 2.5 |
| Distearoylethylhydroxyethylmethylammonium methosulphate at 75% by weight in stearyl alcohol, sold under the trade name Dehyquart F75 by the company Cognis | 2.5 | 2.5 | 2.5 |
| Lauryl PEG/PPG-18/18 methicone at 72% by weight of active material, sold under the trade name Dow Corning 5200 formulation aid by the company Dow Corning (viscosity 2750 mm$^2$/s) | 1 | 1 | 1 |
| Citric acid monohydrate | 0.85 | 0.85 | 0.85 |
| Preservative, fragrance | qs | qs | qs |
| Deionized water | qs 100 | qs 100 | qs 100 |

Compositions A, B and C according to the invention exhibit good properties in terms of smoothing the hair fibre during rinsing and on dried hair.

The above written description of the invention provides a manner and process of making and using it such that any person skilled in this art is enabled to make and use the same, this enablement being provided in particular for the subject matter of the appended claims, which make up a part of the original description.

As used herein, the phrases "selected from the group consisting of," "chosen from," and the like include mixtures of the specified materials. Terms such as "contain(s)" and the like as used herein are open terms meaning 'including at least' unless otherwise specifically noted. The term "mentioned" notes exemplary embodiments, and is not limiting to certain species. As used herein the words "a" and "an" and the like carry the meaning of "one or more." Where a modifying term is contained in parentheses, such as "(uncrosslinked) amphiphilic polymer," two things are described, one with the modifying term and one without the modifying term.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. In this regard, certain embodiments within the invention may not show every benefit of the invention, considered broadly.

The invention claimed is:

1. A composition comprising, in an aqueous medium:
   0.1% to 20% by weight of one or more volatile linear alkanes comprising from 7 to 15 carbon atoms,
   0.5% to 25% by weight of one or more silicones having a viscosity of greater than or equal to 20 000 mm$^2$/s at 25° C.,
   one or more non-silicone fatty substances different from the volatile linear alkanes, wherein the weight ratio of the amount of said non-silicone fatty substance(s) to the amount of said silicone(s) is from 0.1 to 5.

2. The composition according to claim 1, wherein the volatile linear alkane is at least one selected from the group consisting of n-heptane (C7), n-octane (C8), n-nonane (C9), n-decane (C10), n-undecane (C11), n-dodecane (C12), n-tridecane (C13), and n-tetradecane (C14).

3. The composition according to claim 1, wherein the volatile linear alkane is at least one selected from the group consisting of n-nonane, n-undecane, n-dodecane, n-tridecane, and n-tetradecane.

4. The composition according to claim 1, wherein the volatile linear alkane is of plant origin.

5. The composition according to claim 1, wherein the volatile linear alkane is present in a content of 1% to 20% by weight relative to the total weight of the composition.

6. The composition according to claim 1, wherein the silicone has a viscosity of greater than 50 000 mm$^2$/s, and less than 200 000 000 mm$^2$/s.

7. The composition according to claim 1, wherein the silicone is at least one selected from the group consisting of:
   (i) a polyalkylsiloxane;
   (ii) a polyarylsiloxane;
   (iii) a polyalkylarylsiloxane;
   (iv) a silicone gum of the silicones (i), (ii) and (iii);
   (v) and a silicone resin.

8. The composition according to claim 7, wherein the silicone is a silicone gum of a polyalkylsiloxane, a polyarylsiloxane, or a polyalkylarylsiloxane.

9. The composition according to claim 8, wherein the silicone gum has a structure selected from the group consisting of
   polydimethylsiloxane,
   poly[(dimethylsiloxane)/(methylvinylsiloxane)],
   poly[(dimethylsiloxane)/(vinylhydrogenosiloxane)],
   poly[(dihydrogenodimethylsiloxane)/(divinylsiloxane)],
   poly[(dimethylsiloxane)/(diphenylsiloxane)],
   poly[(dimethylsiloxane)/(phenylmethylsiloxane)],
   poly[(dimethylsiloxane)/(diphenylsiloxane)/(methylvinylsiloxane)];
   and mixtures thereof.

10. The composition according to claim 1, wherein the silicone is present in a content of 0.1% to 10% by weight relative to the total weight of the composition.

11. The composition according to claim 1, wherein the non-silicone fatty substance different from the volatile linear alkane is chosen selected from the group consisting of a $C_8$-$C_{40}$ fatty alcohol, an ester of a $C_7$-$C_{39}$ fatty acid, an ester of a $C_8$-$C_{40}$ fatty alcohol, a wax, a plant oil, an animal oil, a mineral oil and a synthetic oil.

12. The composition according to claim 1, wherein the non-silicone fatty substance different from the volatile linear alkane is a fatty alcohol of formula R'OH, where R' denotes a linear or branched, saturated or unsaturated radical containing from 8 to 40 carbon atoms.

13. The composition according to claim 12, wherein the fatty alcohol is at least one selected from the group consisting of lauryl alcohol, myristyl alcohol, cetyl alcohol, stearyl alcohol, cetylstearyl alcohol, oleyl alcohol, behenyl alcohol, hexyldecanol, 2-octyldodecanol, and mixtures thereof.

14. The composition according to claim 1, wherein the fatty substance different from the volatile linear alkanes is present in a content ranging from 0.5% to 25% by weight relative to the total weight of the composition.

15. The composition according to claim 1, further comprising at least one cationic polymer and/or at least one cationic surfactant.

16. A method for the treatment of a keratin material, comprising the application of the composition according to claim 1 to the keratin materials.

17. The method according to claim 16, wherein the keratin material is hair.

18. The composition according to claim 7, wherein the silicone is a polyalkylsiloxane selected from the group consisting of a linear polydimethylsiloxanes with a trimethylsilyl end group, and a polydimethylsiloxanes with a hydroxydimethysilyl end group.

19. The composition according to claim 1, wherein the weight ratio of the amount of said non-silicone fatty substance(s) to the amount of said silicone(s) is from 0.1 to 3.

20. The composition according to claim 1, wherein the composition comprises at least two volatile linear alkanes comprising from 7 to 15 carbon atoms.

* * * * *